United States Patent

Matsuura et al.

[11] Patent Number: 4,467,112
[45] Date of Patent: Aug. 21, 1984

[54] PROCESS FOR PRODUCING P-N-ALKYLBENZOIC ACID

[75] Inventors: Ryo Matsuura, Yamato; Kazuya Nagaoka, Yokohama; Kouji Kusabe, Kamakura; Shuichi Nakatani, Yokohama, all of Japan

[73] Assignee: Kawasaki Kasei Chemicals Ltd., Tokyo, Japan

[21] Appl. No.: 112,710

[22] Filed: Jan. 16, 1980

[30] Foreign Application Priority Data

Jan. 30, 1979 [JP] Japan ............................. 9825

[51] Int. Cl.$^3$ ............................. C07C 51/337
[52] U.S. Cl. ............................. 562/493; 562/459
[58] Field of Search ............................. 562/493

[56] References Cited

PUBLICATIONS

Cran et al., Organic Chemistry 2nd ed., p. 567, (1962).
House, Modern Synthetic Reactions, pp. 173, 232–235, (1972).
Weygand et al., *Preparative Organic Chemistry*, pp. 32–36, 71–76, 986–987, (1972).
Horning et al., Org. Sym. 31, p. 56, (1951).
Wojcik et al., J.A.C.S. 56, 2424–2425, (1934).

*Primary Examiner*—Robert Gerstl
*Attorney, Agent, or Firm*—Oblon, Fisher, Spivak, McClelland & Maier

[57] ABSTRACT p-n-Alkylbenzoic acids having high purity without containing isomers are important as intermediates for liquid crystals. The p-n-alkylbenzoic acid is produced by reacting a p-formylbenzoic acid or its ester with a ketone having the formula

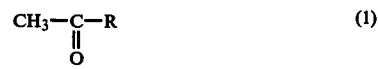

(1)

wherein R represents a $C_1$–$C_{18}$ n-alkyl or n-alkenyl group in the presence of a basic catalyst to obtain an unsaturated ketone compound having the formula

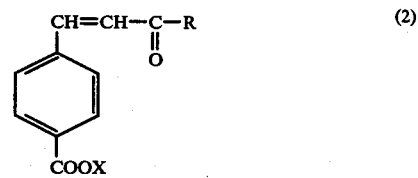

(2)

wherein R is defined above and X represents hydrogen atom or a $C_1$–$C_6$ alkyl group, and then, hydrogenating and reducing the unsaturated ketone compound to obtain the p-n-alkylbenzoic acid having the formula

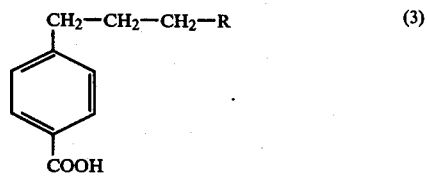

(3)

6 Claims, No Drawings

PROCESS FOR PRODUCING P-N-ALKYLBENZOIC ACID

BACKGROUND OF THE INVENTION

1. Field of the Invention

The present invention relates to a novel, economical, industrial process for producing p-n-alkylbenzoic acids which are important intermediates for liquid crystals.

2. Description of the Prior Arts

It is quite important to obtain a p-n-alkylbenzoic acid, nevertheless it has been quite difficult to attain an economical industrial process for producing p-n-alkylbenzoic acid because branched alkylbenzoic acids or o- or m-alkylbenzoic acids or other by-products are produced.

Heretofore, the conventional processes for producing p-n-alkylbenzoic acids are as follows.

(1) Benzene is acylated with n-aliphatic acid chloride by Friedel-Craft reaction to obtain n-alkylphenyl ketone and then, carbonyl group of the ketone is reduced to obtain n-alkylbenzene and then, n-alkylbenzene is converted into p-n-alkylacetophenone by reacting acetyl chloride and acetyl group of the resulting p-n-alkylacetophenone is oxidized by an oxidizing agent such as hypobromite to obtain p-n-alkylbenzoic acid as disclosed in U.S. Pat. No. 3,683,040, U.S. Pat. No. 3,697,594, U.S. Pat. No. 3,764,621 and U.S. Pat. No. 2,383,874;

(2) p-n-Alkylaniline is converted into p-n-alkylbenzonitrile by diazotizing it and reacting with an aqueous solution of cuprous cyanide and then p-n-alkylbenzonitrile is hydrolyzed into p-n-alkylbenzoic acid as disclosed in Japanese Unexamined Patent Publication No. 73384/1973;

(3) n-Alkylbenzene is converted into p-n-alkylbenzoic acid with oxalic dichloride by Friedel-Craft reaction as a special method.

In accordance with these conventional processes, the reaction steps are complicated and much and cause many side-reactions and a separation of isomers is not easy and moreover, large amounts of expensive reagents such as aluminum chloride are required and a treatment of waste drainages is not easy, and the resulting p-n-alkylbenzoic acid is expensive.

SUMMARY OF THE INVENTION

It is an object of the present invention to provide a process for producing a novel economical, industrial process for producing p-n-alkylbenzoic acid without disadvantages caused in the conventional processes.

The foregoing and other objects of the present invention have been attained by producing p-n-alkylbenzoic acid which comprises reacting p-formylbenzoic acid or its ester with a ketone having a formula

   (1)

wherein R represents a $C_1$-$C_{18}$ n-alkyl or n-alkenyl group in the presence of a basic catalyst to produce an unsaturated ketone compound having the formula

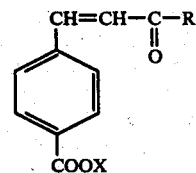

wherein R is defined in the formula (1) and X represents hydrogen atom or a $C_1$-$C_6$ alkyl group, and then reducing the unsaturated ketone group of the unsaturated ketone compound.

In the optimum process, the unsaturated ketone compound (2) is hydrogenated and reduced by Wolff-Kishner reduction or other reduction for a ketone group.

DETAILED DESCRIPTION OF THE PREFERRED EMBODIMENTS

The process of the present invention has two steps which include the reaction for producing an unsaturated ketone compound (2) by reacting p-formylbenzoic acid or its ester with methyl n-alkyl ketone; and a reduction for producing the object p-n-alkylbenzoic acid by reducing the unsaturated ketone group of the unsaturated ketone compound (2) to a n-alkyl group. However, in both of the first and second steps of the reactions, the formations of intermediates are considered. Therefore, it is possible to complete the reactions in the second and third steps.

The first step of the reaction is considered to be performed by the following reactions.

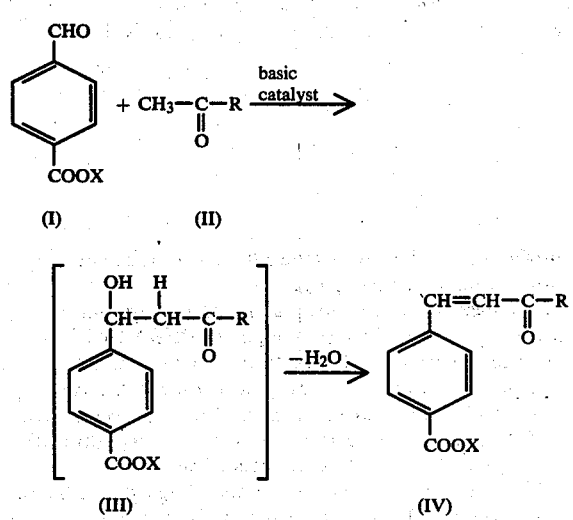

(R and X are defined above).

In the first step, the intermediate (III) is produced by reacting p-formylbenzoic acid (hereinafter referring to as PFBA) or its ester (I) with the ketone (II) in the presence of the basic catalyst, and then, the intermediate (III) is dehydrated by the post-treatment of the reaction mixture to produce the unsaturated ketone compound (IV) and the product (IV) is recovered.

The starting materials used in the first step of the present invention are PFBA or its esters which are preferably methyl esters obtained as by-products from the step of producing dimethyl terephthalate as a starting material of polyesters. The starting material also can be obtained by a liquid phase oxidation of p-xylene, a hydrolysis of a product obtained by a chlorination of p-xylene, or a hydrolysis of a product obtained by a chlorination of p-toluic acid. The resulting PFBA can be esterified to obtain the esters. The esters are preferably a $C_1$–$C_6$ alkyl esters especially methyl ester which is industrially available and economical.

Suitable ketones (II) as the starting material used in the first step of the present invention include methyl n-alkyl ketones having the formula (II) wherein R is a $C_1$–$C_{18}$ n-alkyl or n-alkenyl group such as methyl, ethyl, n-propyl, n-butyl, n-heptyl, n-octyl, n-decyl, n-dodecyl, n-hexadecyl, n-octadecyl, ethenyl, n-propenyl, n-butenyl, n-heptenyl, n-octenyl, n-decenyl, n-dodecenyl, n-hexadecenyl, n-octadecenyl groups.

In the first step, the ketone (II) is used at a molar ratio of 1 to 100 to PFBA or its ester (I) as the starting material and usually a weight ratio of 1 to 20 to PFBA or its ester (I). When the ratio of the ketone (II) to PFBA or its ester (I) is not enough, a side-reaction is easily formed. Therefore, excess of the ketone (II) is preferably used as a solvent. When the ketone (II) is acetone, it is especially preferable to use large excess of acetone as the solvent. Thus, it is possible to use the other organic solvents such as alcohols, aromatic hydrocarbons, aliphatic hydrocarbons, alicyclic hydrocarbons, heterocyclic compounds as a diluent for the ketone (II).

In the first step, the basic catalyst is used. Suitable basic catalysts include alkali metal hydroxides such as sodium hydroxide and potassium hydroxide; alkali metal carbonates such as sodium carbonate and potassium carbonate; organic bases such as amines such as trimethylamine, triethylamine, tripropylamine, diethylamine, piperidine; quaternary ammonium hydroxides such as trimethyl benzylammonium hydroxide:

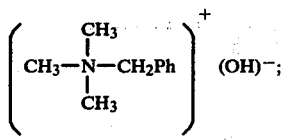

alcoholates such as sodium methylate and sodium ethylate; and basic ion exchange resins.

The basic catalyst is used at a catalytic amount and is a rate of 0.05 to 100% by weight to PFBA or its ester. In order to control the catalytic activity of the basic catalyst and to prevent a polymerization of the ketone, it is preferable to add water in the reaction system, preferably at a ratio of less than 100% by weight to the ketone especially in the case of acetone.

The reaction temperature is depending upon the kind and amount of the basic catalyst and is usually in a range of 0° C. to a boiling point preferably 0° C. to 50° C.

The reaction time is depending upon the reaction temperature and the amount of the basic catalyst and is usually enough to be shorter than about 5 hours at a room temperature.

In the first step, the post-treatment of the reaction mixture containing the resulting intermediate in the reaction can be carried out as follows.

A mineral acid such as hydrochloric acid or sulfuric acid is added to the reaction mixture to cause an acidic condition. The reaction mixture is preferably heated to result in a dehydration of the intermediate (III) and then, the solvent is distilled off from the reaction mixture or the reaction mixture is diluted with water and the product is separated by a filtration to obtain the unsaturated ketone compound (IV).

The resulting unsaturated ketone compound (IV) having the formula (2) is used for the reduction in the second step if necessary, after purifying it by a suitable purification such as a recrystallization from a suitable solvent such as an alcohol.

The reduction in the second step is considered to perform as follows:

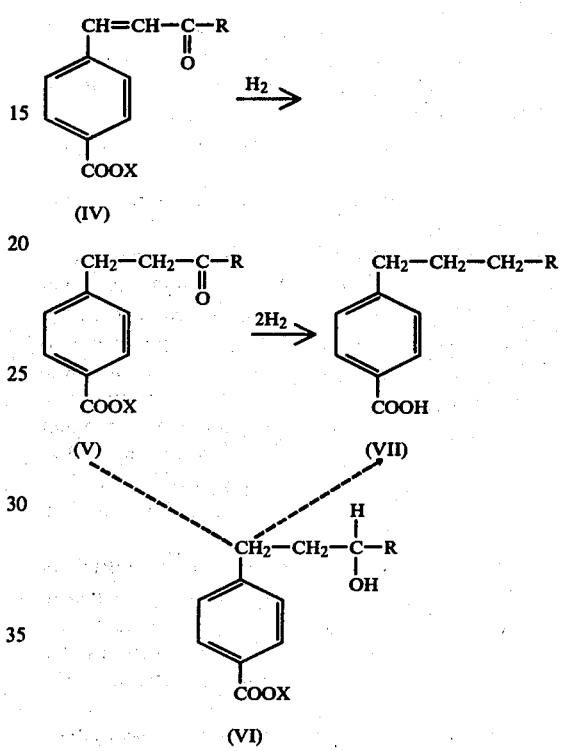

(A salt form is also shown in the acid form).

In the reduction as the second step, it is preferable that —CH=CH— group of the unsaturated ketone compound (IV) obtained in the first step is hydrogenated to produce the saturated ketone compound (V) as the intermediate, and then, the ketone group is reduced to produce the object p-n-alkylbenzoic acid (VII).

Thus, the reduction as the second step can be carried out by one of the following three processes.

1 As the optimum process, —CH=CH— group of the unsaturated ketone group of the unsaturated ketone compound (IV) is hydrogenated by a catalytic reduction to produce a saturated ketone compound (V) and then, the ketone group of the compound (V) is reduced with hydrazine by Wolff-Kishner reduction. In accordance with this process, the operation is easy and the yield is high.

2 The unsaturated ketone compound (IV) is directly reduced to p-n-alkylbenzoic acid (VII) without forming the saturated ketone compound (V) as the intermediate. Clemmensen reduction using metal amalgam such as zinc amalgam can be applied for this process.

3 The saturated ketone compound (V) as the intermediate is produced by the hydrogenation and then, it is further reduced with lithium-aluminum hydride, sodium or by a catalytic hydrogenation in the presence of Raney nickel catalyst, to produce a hydroxy compound (VI) as the intermediate and the compound (VI) is further reduced by a known method such as a combination of a dehydration and hydrogenation.

The reduction can be also carried out by the other processes such as using a combination of a mineral acid and a metal such as zinc or tin or a combination of hydrogen iodide and phosphorus.

The embodiment of the reduction 1 will be described in detail.

In order to produce the saturated ketone compound (V) as the intermediate by a hydrogenation of —CH=CH— group of the unsaturated ketone compound (IV), it is preferable to carry out a catalytic reduction. The catalyst can be suitable known catalyst such as paradium-carbon (Pd-C), platinum black (Pt), Raney nickel (R-Ni), and, rhodium-carbon (Rh-C). The rhodium-carbon catalyst is the optimum. The amount of the catalyst is usually at a ratio of 0.01 to 10% by weight to the starting material.

The reaction temperature is usually in a range of $-20°$ C. to $100°$ C. especially $0°$ C. to $50°$ C. The pressure of hydrogen is usually in a range of the atmospheric pressure to 50 kg/cm$^2$, preferably the atmospheric pressure to 10 kg/cm$^2$.

The solvent is preferably stable in the reaction condition. Suitable solvents include alcohols such as methanol and ethanol; ketones such as acetone; aliphatic hydrocarbons such as n-hexane; and aromatic hydrocarbons such as benzene, toluene and xylene.

The amount of the solvent to the unsaturated ketone compound (IV) can be enough to make a slurry or the dip the compound (IV), since the solubility of the reaction product is increased in the reaction. Therefore, the amount of the solvent is usually at a ratio of 2 to 30 preferably 5 to 20 times by weight to the compound (IV).

In the catalytic reduction, under said condition, an autoclave equipped with a hydrogen gas feeding tube, a pressure meter, a thermometer, and a stirrer is used as an apparatus and a desired amount of hydrogen gas is absorbed under a desired pressure at a desired temperature with stirring. In usual, when the absorption of hydrogen gas is stopped, the pressure in the autoclave is decreased and nitrogen gas is fed to purge it and if necessary, the catalyst is separated from the reaction mixture and the solvent is separated to obtain the intermediate compound (V) as the residue. It is confirmed by IR spectrum after converting the product into an acid form by a hydrolysis with methanol-water-alkaliaqueous solution, that the intermediate compound (V) is the saturated ketone compound having the formula

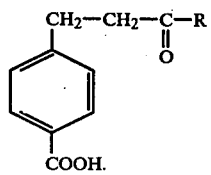

The compound (V) can be the acid form or the ester form as the starting material in the following reduction.

In order to obtain the object p-n-alkylbenzoic acid (VII), by reducing ketone group of the saturated ketone compound (V) as the intermediate, it is possible to apply a severe hydrogenation such as Clemmensen reduction. Thus, it is especially effective to apply Wolff-Kishner reduction using hydrazine and a basic catalyst. The basic catalyst used in the Wolff-Kishner reduction can be sodium metal, an alkali metal hydroxide such as sodium hydroxide and potassium hydroxide; and alcoholates such as sodium ethylate. In the reduction, the solvent can be glycols such as ethyleneglycol; alkanolamines such as triethanolamine; cellosolves such as monomethyl or mono-ethyl ethers of ethyleneglycol.

In the Wolff-Kishner reduction of the saturated ketone compound (V), the compound (V), the solvent (5 to 20 times by weight of the compound (V)), hydrazine (molar ratio of 1 to 5 to the compound (V)), and the basic catalyst such as potassium hydroxide (molar ratio of 1.5 to 6 to the compound (V)), are charged into a reactor and the mixture is heated at $50°$ to $250°$ C. preferably $100°$ to $200°$ C. with stirring. Nitrogen gas is generated by the reaction. After the reaction, the reaction mixture is cooled and an alkali metal salt of p-n-alkylbenzoic acid can be precipitated in the reactor. When the reaction mixture is acidified by itself or after diluting it with water, and the product is separated by a filtration and dried, a crude crystal of p-n-alkylbenzoic acid (VII) can be obtained. If necessary, the crude crystal can be purified by a recrystallization or a distillation. The acid for the acidification can be an acid having an acidity for an acidic precipitation of the compound (VII) and usually a mineral acid such as hydrochloric acid and sulfuric acid or an organic acid such as acetic acid.

The p-n-alkylbenzoic acid obtained by the process of the present invention has high purity without containing o- or m-isomer to be different from the product obtained by the conventional process. In IR spectrography of the product obtained by the process of the present invention, any spectrum for the impurity is not found.

In accordance with the process for producing p-n-alkylbenzoic acid of the present invention, a formation of a by-product of an isomer as formed in the conventional process is not found to easily obtain the product having high purity. Moreover, it is unnecessary to use aluminum chloride and bromine water which are expensive and not easily post-treated though the conventional process needs large quantities. Therefore, the process of the present invention is remarkably advantageous as an industrial value such as easy operation and economical one in comparison with the conventional process.

In a preparation of a liquid crystal, a contamination of an isomer such as o- or m-alkylbenzoic acid or branched alkylbenzoic acid is fatal. It is quite important to obtain p-n-alkylbenzoic acid having high purity. It has been succeeded to obtain such product by the process of the present invention.

The present invention will be illustrated by certain examples and references which are provided for purposes of illustration only and are not intended to be limiting the present invention.

EXAMPLE 1

Into a 1 liter four necked flask equipped with a condenser, a dropping funnel, a thermometer and a stirrer, 50 g of PFBA methyl ester, 500 ml. of acetone and 100 ml. of water were charged and the mixture was stirred at a room temperature (about $20°$ C.) and 3 ml. of 40% methanol solution of trimethyl benzylammonium hydroxide as a basic catalyst was gradually added dropwise during 1 hour. The reaction was an exothermic reaction and accordingly, the reaction was carried out under cooling at a room temperature for 2 hours. After the reaction, a dilute hydrochloric acid was added to the reaction mixture to be acidic condition. Acetone was distilled off on a hot water bath to obtain 64 g of a yellowish crude crystal. The crude product was recrystallized from 4 times of methanol to obtain 57.6 g of a purified crystal.

The resulting purified crystal was pale yellowish white and had a melting point of 114° to 116° C. It was confirmed by NMR, IR and an elementary analysis, that the product is methyl p-(3-oxo-1-butenyl)benzoate:

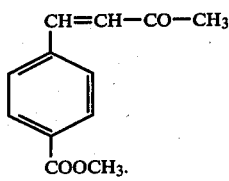

The yield of the purified crystal based on the starting material of PFBA methyl ester was 92.5 mole %.

EXAMPLE 2

In accordance with the process of Example 1 except using 20 ml. of 10% aqueous solution of sodium hydroxide instead of the solution of trimethyl benzylammonium hydroxide, the reaction and the treatment were carried out to obtain 64 g of a crude crystal. In accordance with the process of Example 1, the purification of the crude crystal was carried out by the recrystallization. The result was the same as that of Example 1.

EXAMPLE 3

Into an autoclave, 10 g of methyl p-(3-oxo-butenyl)-benzoate (hereinafter p-(3-oxo-butenyl)benzoic acid is referred to as POBBA) obtained in Example 1, and 100 ml. of methanol and 0.3 g of 5% Pd-C (Pd carried on active carbon) as a catalyst were charged and the autoclave was purged with nitrogen and hydrogen gas was fed at a room temperature under a pressure of 3 kg/cm$^2$G to carry out a hydrogenation. The absorption of hydrogen gas was finished after about 30 minutes. After the reaction, the catalyst was separated by a filtration and 200 ml. of 10% aqueous solution of sodium hydroxide was added and the mixture was refluxed for 1 hour. Then, most of methanol was distilled off under a reduced pressure. Hydrochloric acid was added to the reaction mixture for an acidic precipitation so as to precipitate a white crystal. The crystal was separated by a filtration and dried to obtain 7.5 g of the product. The filtrate was extracted three times with chloroform to recover 1.3 g of a residual product remained in the filtrate. The product had a melting point of 119° to 120° C. It was confirmed by NMR, IR and an elementary analysis, that the product is p-(3-oxo-n-butyl)benzoic acid:

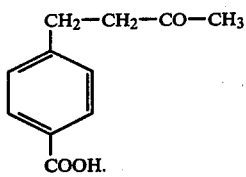

The yield of the product based on the starting material of POBBA methyl ester was 93.5 mole %.

EXAMPLE 4

Into a four necked flask equipped with a separating tube for evaporated water, a thermometer and a stirrer, 5 g of p-(3-oxo-n-butyl) benzoic acid obtained in Example 3, 28 g of triethanolamine, 3.6 g of hydrazine hydrate and 5.5 g of potassium hydroxide as a basic catalyst were charged and the mixture was heated with stirring. Nitrogen gas was initially generated at higher than 100° C. especially about 125° C. and vigorously generated at about 140° C. When the generation of nitrogen gas was reduced, the temperature of the mixture was gradually elevated under evaporating water in the system to reach at about 200° C. after about 5 hours. The reaction mixture was a transparent yellowish liquid. The reaction mixture was poured into 400 ml. of water and hydrochloric acid was added to be acidic condition so as to precipitate a white precipitate. The precipitate was separated by a filtration and washed with water and dried to obtain 3.5 g of a crystal. The crystal had a melting point of 95° to 114° C. in a liquid crystal form. It was confirmed by NRM, IR and an elementary analysis, that the product is p-n-butylbenzoic acid containing no impurity. The data of the elementary analysis corresponded to the calculated data.

|                | C     | H    | O     |
|----------------|-------|------|-------|
| Found (%)      | 74.12 | 7.90 | 17.98 |
| Calculated (%) | 74.17 | 7.86 | 17.97 |

The yield of the product based on the starting material of p-(3-oxo-n-butyl) benzoic acid was 75.5 mole %. It was confirmed that both were identical by comparisons of NMR, IR and a mixed examination with a p-n-butyl benzoic acid as a commercially available p-n-butylbenzoic acid (Kanto Kagaku K.K.) as an intermediate for a liquid crystal.

EXAMPLE 5

(1) Reaction of PFBA methyl ester with methyl ethyl ketone:

In accordance with the process of Example 1 except using methyl ethyl ketone (no water) instead of acetone, and reacting at 40° C. instead of the room temperature, the reaction and the treatment were carried out to obtain 64 g of a yellowish liquid product. The product was recrystallized from 4 times of methanol to obtain 39 g of a purified product. The resulting purified crystal had a melting point of 95° to 97° C. It was confirmed, by NRM, IR and an elementary analysis, that the product is methyl p-(3-oxo-1-pentyl) benzoate. The yield of the purified crystal based on the starting material of PFBA methyl ester was 58.7 mole %.

(2) Hydrogenation of methyl p-(3-oxo-1-pentenyl)benzoate (p-(3-oxo-1-pentenyl) benzoic acid is referred to as POPBA):

In accordance with the process of Example 3 except using POPBA methyl ester instead of POBBA methyl ester, a hydrogenation was carried out and the product was separated by a filtration and dried to obtain 7.8 g of the product. An amount of the product obtained by an extraction from a filtrate was 1.0 g. The product had a melting point of 105° to 117° C. It was confirmed, by NMR, IR and an elementary analysis, that the product is p-(3-oxo-n-pentyl) benzoic acid. The yield of the product based on the starting material of POPBA methyl ester was 93.1 mole %.

(3) Wolff-Kishner reduction of p-(3-oxo-n-pentyl) benzoic acid:

In accordance with the process of Example 4 except using p-(3-oxo-n-pentyl) benzoic acid instead of p-(3-oxo-n-butyl) benzoic acid, the reaction and the treatment were carried out to obtain 3.5 g of the crystal. The resulting crystal had a melting point of 89° to 126° C. in a liquid crystal form. It was confirmed by NMR, IR and an elementary analysis that the product is p-n-pentylbenzoic acid containing no impurity. The data of the elementary analysis correspond to the calculated data.

|  | C | H | O |
| --- | --- | --- | --- |
| Found (%) | 75.08 | 8.30 | 16.62 |
| Calculated (%) | 75.02 | 8.33 | 16.65 |

The yield of the crystal based on the starting material of p-(3-oxo-n-pentyl) benzoic acid was 75.1 mole %. It was confirmed that both were identical by comparisons of NMR, IR and a mixed examination with a p-n-pentylbenzoic acid as a commercially available p-n-pentylbenzoic acid (Kanto Kagaku K.K.) as an intermediate for a liquid crystal.

EXAMPLE 6

(1) Reaction of PFBA methyl ester with n-butyl ketone:

In accordance with the process of Example 5-(1) except using methyl n-butyl ketone instead of methyl ethyl ketone, the reaction and the treatment were carried out to obtain 52 g of a purified product. The product had a melting point of 98° to 98.5° C. It was confirmed by NMR, IR and an elementary analysis, that the product is methyl p-(3-oxo-1-heptenyl) benzoate:

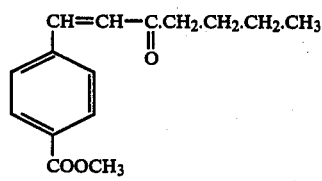

The yield of the purified crystal based on the starting material of PFBA methyl ester was 69.3 mole %.

(2) Hydrogenation of methyl p-(3-oxo-1-heptenyl) benzoate (POHBA methyl ester) and Wolff-Kishner reduction of the product:

Into an autoclave, 10 g of POHBA methyl ester, 100 ml. of methanol and 0.3 g of 5% Pd-C(Pd carried on active carbon) as a catalyst were charged and the autoclave was purged with nitrogen and hydrogen gas was fed at a room temperature under a pressure of 3 kg/cm$^2$G to carry out a hydrogenation. The absorption of hydrogen gas was finished after 1.5 hours. After the reaction, the catalyst was separated by a filtration and the solvent was distilled off from the filtrate to obtain a yellowish oily product as a residue.

Into a four necked flask equipped with a separating tube for evaporated water, a thermometer and a stirrer, the oily product, 57 g of triethanolamine, 6.7 g of hydrazine hydrate and 10.3 g of potassium hydroxide as a basic catalyst were charged and the mixture was heated with stirring. Nitrogen gas was initially generated at higher than 100° C. especially about 125° C. and vigorously generated at about 140° C. When the generation of nitrogen gas was reduced, the temperature of the mixture was gradually elevated under evaporating water in the system to reach at about 200° C. after about 5 hours. The reaction mixture was a transparent yellowish liquid. The reaction mixture was poured into 800 ml. of water and hydrochloric acid was added to be an acidic condition so as to precipitate a white precipitate. The precipitate was separated by a filtration and washed with water and dried to obtain 6.3 g of a crystal. The crystal had a melting point of 101° to 120° C. in a liquid crystal form. It was confirmed by NMR, IR and an elementary analysis, that the product is p-n-heptylbenzoic acid. The data of the elementary analysis correspond to the calculated data.

|  | C | H | O |
| --- | --- | --- | --- |
| Found (%) | 76.33 | 9.10 | 14.57 |
| Calculated (%) | 76.36 | 9.09 | 14.55 |

The yield of the product based on the starting material of POHBA methyl ester was 70.3 mole %. It was confirmed that both were identical by comparisons of NMR, IR and a mixed examination with a p-n-heptylbenzoic acid as a commercially available p-n-heptylbenzoic acid (Kanto Kagaku K.K.) as an intermediate for a liquid crystal.

EXAMPLE 7

In accordance with the process of Example 6 (1) and (2) except using methyl n-propyl ketone (MPK) or methyl n-amyl ketone (MAK), the reaction and the treatment were carried out to obtain methyl p-(3-oxo-n-hexenyl) benzoate or methyl p-(3-oxo-n-octenyl) benzoate and further the reaction and the treatment were carried out to obtain p-n-hexylbenzoic acid or p-n-octylbenzoic acid. The melting points, NMR, IR and elementary analyses of the product were compared with those of the commercially available products. The results are shown in Table.

TABLE

| Ketone | MPK | MAK |
| --- | --- | --- |
| Methyl p-(3-oxo-n-alkenyl)benzoate |  |  |
| Product | methyl p-(3-oxo-n-hexenyl) benzoate | methyl p-(3-oxo-n-octenyl) benzoate |
| Yield *1 (mole %) | 70.7 | 40.4 |
| Melting point (°C.) | 101.5~102 | 99.5~100 |
| p-n-Alkylbenzoic acid |  |  |
| Product | p-n-hexylbenzoic acid | p-n-octylbenzoic acid |
| Yield *2 (mole %) | 70.9 | 71.1 |
| Melting point (°C.) | 96~111 | 97~110 |

Note:
*1: yield based on PFBA methyl ester
*2: yield based on methyl p-(3-oxo-n-alkenyl)benzoate

EXAMPLE 8

(1) Reaction of PFBA with methyl n-butyl ketone:

Into a 2 liter four necked flask equipped with a condenser, a dropping funnel, a thermometer and a stirrer, 50 g of PFBA and 1000 ml. of methyl n-butyl ketone were charged and the mixture was stirred at a room temperature and 40 g of piperidine as a basic catalyst was added and the mixture was heated to 50° C. and the reaction was continued at the same temperature for 3 hours. The unreacted PFBA was disappeared. The speed for producing the object compound was analyzed by a gas chromatography. After the reaction, the reaction mixture was concentrated under a reduced pressure to obtain a white crystal. The crystal was dispersed into hot water and hydrochloric acid was added to be acidic condition, and the product was separated by a filtration and dried to obtain 76 g of a crude crystal. The crude crystal was recrystallized from methanol. It was confirmed by IR and NMR that the product was p-(3-oxo-n-heptenyl) benzoic acid. The recrystallized product was esterified to obtain methyl ester thereof and IR was compared and a mixed examination was carried out in accordance with the test of Example 6-(1). As a result, it was confirmed that both were identical.

(2) Hydrogenation of p-(3-oxo-1-heptenyl) benzoic acid (POHBA) and Wolff-Kishner reduction of the product:

Into an autoclave, 10 g of POHBA, 300 ml. of ethanol and 1.0 g of 5% Rh-C (Rh carried on active cargon) as a catalyst were charged and the autoclave was purged with nitrogen and hydrogen gas was fed at a room temperature under a pressure of 10 kg/cm$^2$G to carry out a hydrogenation. The absorption of hydrogen gas was finished after about 4 hours. After the reaction, the catalyst was separated by a filtration and the solvent was distilled off under a reduced pressure to obtain 10 g of a white product.

In accordance with the Wolff-Kishner reduction of Example 6-(2) except using the product, 57 g of ethyleneglycol, 6.5 g of hydrazine hydrate and 10.2 g of potassium hydroxide as a basic catalyst and reacting at lower than 170° C., the reduction was carried out to obtain 9.0 g of a crude crystal, and 5 g of the crude crystal was recrystallized from n-hexane to obtain 4 g of a purified product. It was confirmed that the product was identical to p-n-heptylbenzoic acid obtained in Example 6-(2). On the other hand, 4.0 g of the crude crystal was purified by a distillation under a reduced pressure of 1 mmHg at a temperature of 152° to 154° C. to obtain 3.2 g of a purified p-n-heptylbenzoic acid.

EXAMPLE 9

In accordance with the process of Example 8 except using acetone instead of methyl n-butyl ketone, the reactions and the treatments were carried out. The results are shown in Table.

| Reaction of PFBA with acetone: | |
|---|---|
| Amount of PFBA: | 50 g |
| Yield of crude p-(3-oxo-n-butenyl) benzoic acid | 59 g |
| Hydrogenation and Reduction: | |
| Amount of crude p-(3-oxo-n-butenyl) benzoic acid | 10 g |
| p-n-Butylbenzoic acid: | |
| Yield of crude product: | 8.4 g |
| Yield of purified product (recrystallization) (5 g of crude product) | 3.2 g |

We claim:

1. A process for producing p-n-alkylbenzoic acid which comprises (1) reacting a p-formylbenzoic acid or its ester with a ketone having the formula

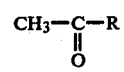

$$CH_3-C-R \qquad (1)$$
$$\parallel$$
$$O$$

wherein R represents a $C_1$-$C_{18}$ n-alkyl or n-alkenyl group in the presence of a basic catalyst to obtain an intermediate reaction product, (2) dehydrating said reaction product in an acidic condition to obtain an unsaturated ketone compound having the formula

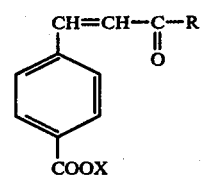

(2)

wherein R is defined above and X represents hydrogen atom or a $C_1$-$C_6$ alkyl group, (3) hydrogenation said unsaturated ketone thereby converting —CH=CH— to —CH$_2$—CH$_2$—, and (4) reducing said resulting ketone thereby converting

$$-C-$$
$$\parallel$$
$$O$$

to —CH$_2$— to obtain the p-n-alkylbenzoic acid having the formula

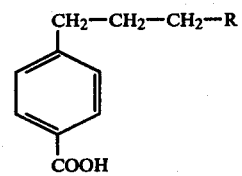

(3)

wherein R is $C_1$-$C_{18}$ n-alkyl.

2. A process according to claim 1 wherein said unsaturated ketone compound (2) is hydrogenated in a solvent in the presence of a hydrogenation catalyst in an autoclave.

3. A process according to claim 2 wherein said hydrogenation product is reduced by hydrazine and a basic catalyst.

4. A process according to claim 1 wherein said p-formylbenzoic acid or its ester is mixed with excess of said ketone (1) for reaction in the presence of said basic catalyst.

5. A process according to claim 1 wherein said basic catalyst is selected from the group consisting of an inorganic alkali metal carbonate or hydroxide, an organic amine, a quaternary ammonium hydroxide, an alkali metal alcoholate, or a basic ion-exchange resin.

6. A process according to claim 1 wherein water is added in the reaction of said p-formylbenzoic acid or its ester with acetone.

* * * * *